United States Patent
Elliott et al.

(10) Patent No.: US 12,257,066 B2
(45) Date of Patent: Mar. 25, 2025

(54) METHOD AND APPARATUS TO MEASURE BONE HEMODYNAMICS AND DISCRIMINATE HEALTHY FROM DISEASED BONE, AND OPEN REDUCTION INTERNAL FIXATION IMPLANT WITH INTEGRATED OPTICAL SENSORS

(71) Applicant: THE TRUSTEES OF DARTMOUTH COLLEGE, Hanover, NH (US)

(72) Inventors: Jonathan Thomas Elliott, Meriden, NH (US); Ida Leah Gitajn, Hanover, NH (US); Shudong Jiang, Hanover, NH (US); Brian Pogue, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 755 days.

(21) Appl. No.: 17/290,991

(22) PCT Filed: Nov. 1, 2019

(86) PCT No.: PCT/US2019/059487
§ 371 (c)(1),
(2) Date: May 3, 2021

(87) PCT Pub. No.: WO2020/092968
PCT Pub. Date: May 7, 2020

(65) Prior Publication Data
US 2022/0096000 A1    Mar. 31, 2022

Related U.S. Application Data

(60) Provisional application No. 62/755,067, filed on Nov. 2, 2018.

(51) Int. Cl.
*A61B 17/80* (2006.01)
*A61B 5/00* (2006.01)

(52) U.S. Cl.
CPC .......... *A61B 5/4504* (2013.01); *A61B 5/0071* (2013.01); *A61B 5/4851* (2013.01); *A61B 17/80* (2013.01)

(58) Field of Classification Search
CPC .... A61B 2560/0214; A61B 2560/0219; A61B 5/1455; A61B 2562/0238; A61B 5/0002;
(Continued)

(56) References Cited

U.S. PATENT DOCUMENTS 9,125,611 B2 * 9/2015 Eaves ................ A61B 6/4441
2002/0002932 A1   3/2002 Arkin
(Continued)

OTHER PUBLICATIONS

International Patent Application No. PCT/US2019/059487 International Search Report and Written Opinion mailed Feb. 21, 2020, 11 pages.

*Primary Examiner* — Deborah L Malamud
(74) *Attorney, Agent, or Firm* — Cozen O'Connor

(57) ABSTRACT

An ORIF implant has an electronics module with a stimulus light and optical sensors for sensing fluorescent emissions coupled to a near-field digital radio. The implant is used with a near-field radio to receive a sequence of fluorescent emissions readings from the implant into a processor that fits the sequence of readings to a bone-specific kinetic model that is a superposition of a plug flow model of periosteal perfusion and a two-compartment model of endosteal perfusion of perfusion of bone. A system for use during ORIF surgery has an injector for fluorescent dye, a camera to send a sequence of images of fluorescent emissions from fluorescent dye in a bone of a subject to an image processor when the bone is illuminated with a stimulus light, the processor configured to fit the sequence of images to a model of perfusion of bone.

7 Claims, 9 Drawing Sheets

(58) Field of Classification Search
CPC ............... A61B 5/0031; A61B 5/0261; A61B
2562/0233; A61B 2034/102; A61B
2034/108; A61B 34/10; A61B 2090/376;
A61B 5/05; A61B 2560/04; A61B
5/0071; A61B 5/24; A61B 2034/101;
A61B 2034/104; A61B 2034/2055; A61B
5/4504; A61B 17/72; A61B 17/80; A61N
1/05; A61N 1/0558
See application file for complete search history.

(56) References Cited

U.S. PATENT DOCUMENTS

| | | |
|---|---|---|
| 2011/0178556 A1 | 7/2011 | Hansson |
| 2012/0148031 A1 | 6/2012 | Eaves |
| 2014/0257291 A1 | 9/2014 | Houff |
| 2017/0007420 A1 | 1/2017 | Stevenson et al. |
| 2017/0084024 A1 | 3/2017 | Gurevich |

* cited by examiner

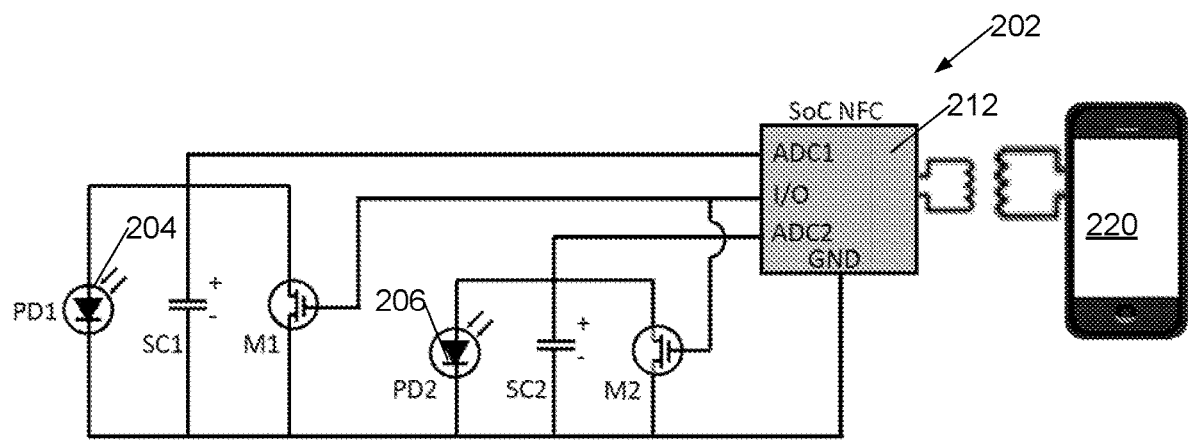
Fig. 3
Fig. 4
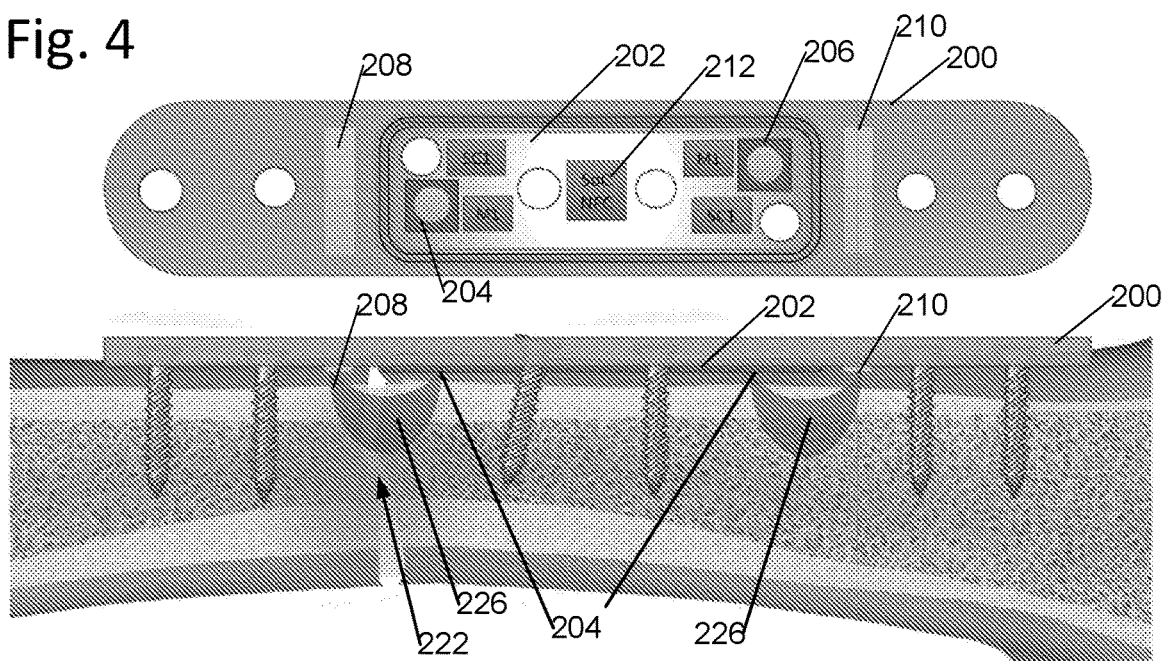
Fig. 5

METHOD AND APPARATUS TO MEASURE BONE HEMODYNAMICS AND DISCRIMINATE HEALTHY FROM DISEASED BONE, AND OPEN REDUCTION INTERNAL FIXATION IMPLANT WITH INTEGRATED OPTICAL SENSORS

PRIORITY CLAIM

The present application is a 35 U.S.C. § 371 filing of International Application No. PCT/US2019/059487 filed Nov. 1, 2019, which claims priority to U.S. Provisional Patent Application No. 62/755,067 filed Nov. 2, 2018. The entire contents of the aforementioned provisional patent application are incorporated herein by reference.

FIELD

The present document relates to the field of methods and equipment for use in orthopedic surgery. Specifically, the present document relates to methods and equipment for assessing perfusion and viability of bone, including, but not limited to, fractured bone requiring surgical repair such as open reduction and internal fixation.

BACKGROUND

Traumatic bone fractures are quite common in the United States. While many of these, particularly in children, can be treated with closed reduction, many fractures—including many comminuted or compound fractures—are treated with open surgical reduction and internal fixation (ORIF). ORIF often involves attaching bone fragments to each other with implanted ORIF implants such as pins, rods, nails, rigid plates, and/or screws that "set" the fracture, preventing relative movement of bone fragments and allowing healing to take place. Fractures treated with ORIF include but are not limited to many but not all comminuted fractures, where fractured bones have fragmented into numerous pieces, open fractures where bone ends have pierced skin and require cleaning and debridement as well as reduction and fixation, and periprosthetic fractures, where bone surrounding an implant has fractured.

Fractures do not always heal well or promptly, common complications include either or both infection and non-union—where bone fragments fail to rejoin. Non-union and infection greatly increase the risk of amputation, additional surgical procedures and extended hospital stays, and represents an important cause of cost/waste/morbidity.

Blood flow to bone may be disrupted by fracture because fractures may disrupt flow to or through vessels within the bone, including arterioles, perforating veins, and Haversian canals, as well as damaging or disrupting the periosteum and its blood supply. Bone deprived of blood flow may become necrotic, and necrotic bone is particularly susceptible to infection. Poorly perfused bone that remains within the setting of open fracture may become a site of biofilm formation and subsequent resistance to antibiotic treatments. Poor perfusion also prevents proper union of the bone and prolongs healing. The current standard-of-care is to monitor patients radiographically for fracture union. Infection is monitored by clinical inspection and evaluation. Failure to treat bone infection results in recurrent infection and dramatically increases the risk of repeat surgical procedures, leading to prolonged morbidity, loss of function and potential loss of limb

SUMMARY

In an embodiment, an implant for open surgical reduction with internal fixation of fractures has an integrated electronics module with optical sensors for sensing luminous emissions, a stimulus light, and a near-field digital radio; the optical sensors are coupled to the near-field digital radio. The implant is used with a near-field radio configured to power and receive data from the implant into a processor to obtain a sequence of fluorescent emissions readings and to fit the sequence of readings to a bone-specific kinetic model comprising a superposition of a plug flow model to model periosteal perfusion and a two-compartment model to model endosteal perfusion model of perfusion of bone.

In an embodiment, a system for use during surgery for open reduction and internal fixation of fractures has an injector to inject fluorescent dye into a subject, a camera configured to provide a sequence of images of fluorescent emissions from fluorescent dye in a bone of a subject to an image processor when the bone is illuminated with a stimulus light to a processor, the processor being configured to fit the sequence of images to a model of perfusion of bone.

A method of evaluating perfusion in a bone exposed within a surgical wound includes applying fluorescent stimulus-wavelength illumination, imaging the surgical wound and the fractured bone with a fluorescent emissions wavelength camera to provide a sequence of fluorescent emissions images; injecting a fluorescent dye into the subject, the sequence of fluorescent emissions images comprising images of wash-in and wash-out of the fluorescent dye; determining an arterial input function (AIF) using a sensor that detects the fluorescent dye; capturing the sequence of fluorescent emissions images in a digital image processor; and fitting parameters of a bone-specific kinetic model comprising a plug flow model to model periosteal perfusion and a two-compartment model to model endosteal perfusion to pixels of the sequence of fluorescent emissions images.

In an embodiment, a method includes implanting an open reduction and internal fixation (ORIF) implant onto a fractured bone of a subject, the ORIF implant comprising an electronics module, allowing the fracture to begin healing, and, using a near-field radio, causing the electronics module to emit fluorescent stimulus-wavelength illumination into a fracture zone of the fractured bone. The method also includes injecting a fluorescent dye into the subject; sensing fluorescence from the fracture zone with a fluorescent emissions wavelength photosensor of the electronics module to provide a sequence of fluorescent emissions readings, where the sequence of fluorescent emissions readings comprises readings of wash-in and wash-out of the fluorescent dye; and fitting parameters of a bone-specific kinetic model comprising a plug flow model to model periosteal perfusion and a two-compartment model to model endosteal perfusion to the sequence of fluorescent emissions readings. In an alternative embodiment, a light-absorbing dye is injected into the subject; the electronics module of the ORIF implant being configured to emit light of a wavelength absorbed by the light-absorbing dye and to use its photosensor to detect changes in absorption of light caused by presence of the light-absorbing dye.

BRIEF DESCRIPTION OF THE DRAWINGS

FIG. 3 is an electrical schematic of a sensor module mounted on the ORIF implant adjacent to the bone.

FIG. 4 is a schematic bottom view of the ORIF implant showing the ORIF implant with sensor module.

FIG. 5 is a cross sectional side view of the ORIF implant and sensor module as mounted to a fractured bone.

FIG. 6A schematically illustrates the compartments of the HyPC model, overlaid onto the bone anatomy and how these compartments relate kinetically.

FIG. 6B illustrates the flow-scaled aggregate impulse residue function used in the HyPC model, showing the parameters recovered: PBF, EBF, $T_P$, $T_E$, $M_P$, $k_2$.

DETAILED DESCRIPTION

Figure 1:
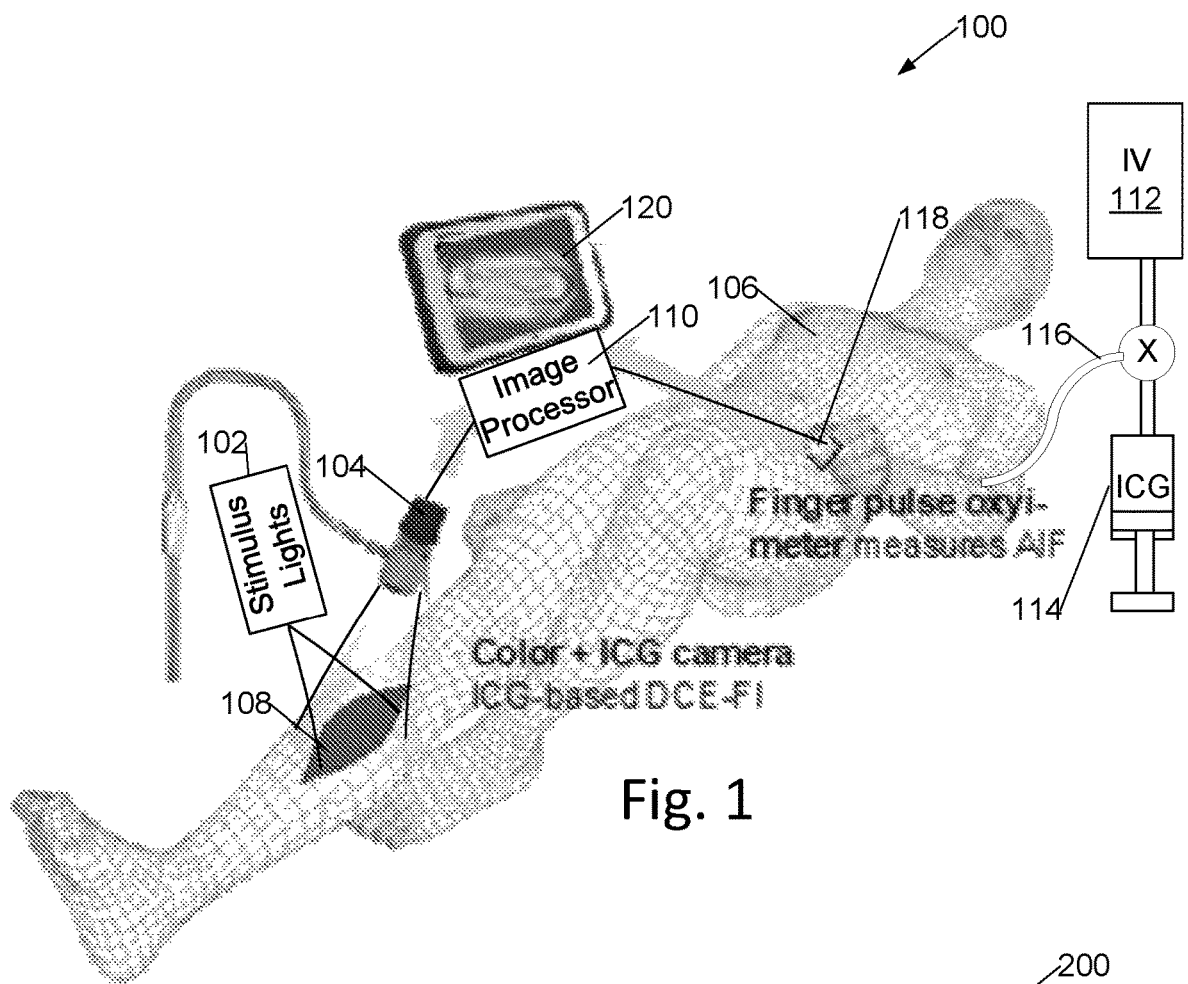
FIG. 1 is a schematic view of the system of the present invention as used to image viability of bone during surgery.

We provide devices and methods to solve an important problem in orthopedic surgery, mainly, how to discriminate between healthy and diseased tissue during debridement and thereupon monitor the healing of a serious fracture after surgery. We provide for measurements of bone blood flow (endosteal blood flow and periosteal blood flow) during open surgery to set a bone fracture. Disruption in blood flow is predictive of non-union (failure of a fracture to heal) and infection. Non-union and infection greatly increase the risk of amputation, second surgery and longer hospital stay, and represents an important cause of cost/waste/morbidity. Post-surgery, we provide an implantable device configured to monitor bone blood flow while the fracture is healing.

This disclosure further quantifies the endosteal and periosteal blood flow using a novel Hybrid Plug-Compartment (HyPC) kinetic model. This is a kinetic model specifically dealing with the two ways bone is supplied with blood flow.

One embodiment 100 (FIG. 1 and FIG. 2) applies the method using fluorescent stimulus lights 102 and fluorescent emissions imaging cameras 104, in some particular embodiments the lights 102 and imaging cameras 104 are separate and in other embodiments they are co-located; the imaging cameras 104 having a direct view of the subject's 106 fractured bone as exposed in a surgical wound 108. An intravenous solution bag 112 provides access to a vein of subject 106, into which an injector 114 provides a bolus of a fluorescent dye such as indocyanine green (ICG) through IV tubing 116 into the subject. Injection of ICG into the subject is detected by a pulse dye densitometer 118, measuring an arterial input function (AIF) that signals a digital image processing unit 110. A time series of fluorescence images of subject's fractured bone 122, as acquired with the imaging camera 104, is transferred to digital image processing unit 110 where the time series of fluorescence images is captured by an image capture unit 124 and saved in an image memory 126, whereupon an image processor 128 is configured by firmware in a memory 142 to, and executes machine readable code of the firmware to perform, an imaging fit using the HyPC model, either on a pixel-by-pixel basis or in an alternative embodiment by averaging over a region of interest, to produce an image of extracted perfusion parameters for display 120; in embodiments the image of extracted perfusion parameters is superimposed on a white-light image of the bone and surgical wound.

Figure 2:
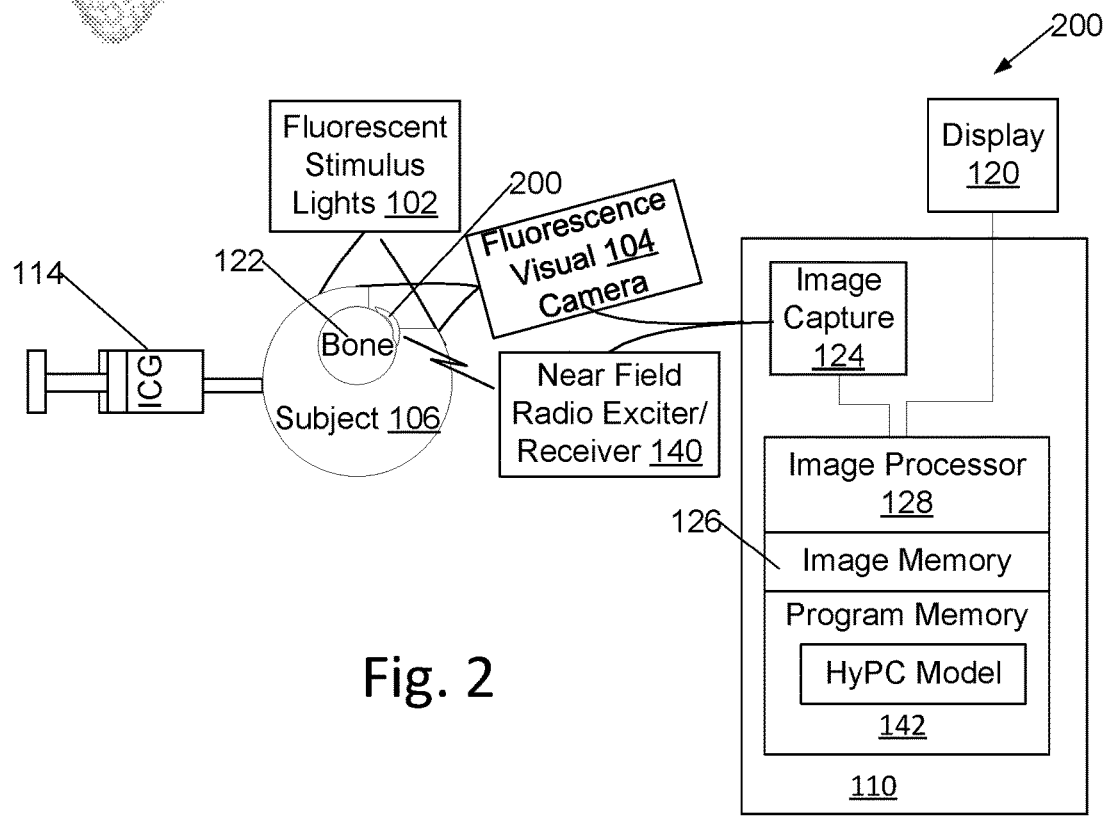
FIG. 2 is a schematic view of the system of the present invention illustrating blocks of the image processing system and showing additional components used to determine perfusion of damaged bone after implantation of an Open Reduction Internal Fixation (ORIF) implant.

In an alternative embodiment an implanted device—an Open Reduction Internal Fixation (ORIF) implant 200 (FIGS. 2-5), typically having form of a rigid plate or rod, with an integrated electronics module 202 having two or more optical sensors 204, 206, two or more phosphorescent stimulus lights 208, 210, and a custom, low-power, system-on-a-chip (SOC), integrated circuit 212 having analog to digital converters coupled to a processor configured to operate the stimulus lights, gather data from the optical sensors 204, 206 and transmit the data using near-field digital radio (NFC) through the subject's skin to external electronics 220. In an embodiment the external electronics includes a smartphone adapted to upload data to image processing system 110 (FIG. 1). In alternative embodiments the external electronics includes a near-field radio exciter/receiver unit 140 that may be coupled to provide data to image processing unit 110. Localized measurements are made from bone periosteum by excitation of phosphorescence sources and detection of photons using implanted PDs during both wash-in and wash-out of dye. In a particular embodiment, the light sources are modulated with a square wave with period greater than 4 phosphorescent lifetimes. This produces a frequency modulated localized emission that is absorbed by local dye in a concentration-dependent manner before being detected by the implant's photodetectors. This signal is read over the near-field communications link to either the smartphone or other near-field excitation/reader unit. The signal is demodulated and converted to dye time-density curves, which are analyzed using the HyPC model given below.

The implant may be made of titanium; however, this metal is conductive and may impair near-field excitation and communications. In embodiments, the implant is made of a polymer such as polyethylene terephthalate glycol-modified (PETG) or ultra-high molecular weight polyethylene (UHMWPE), a material that is currently used in some orthopedic implants. UHMWPE has good transmission of light between 400 and 1000 nm. With polymeric implants, we don't expect any effect of the implant on induction of the near-field communications.

When evaluation of blood flow in a region 222 of healing fracture is required, near field radio 106, 220 is activated to power electronics module 202 and injector 114, which may be a syringe or a pump, injects a bolus of fluorescent dye into subject 106, the bolus is sensed by pulse dye densitometer 118, measuring an arterial input function (AIF). Fluorescent illuminators 208, 210, which may be phosphorescent or light-emitting diode (LED) illuminators, turn on transmitting light into the bone, including the region 222 of fracture. Data is acquired through photodetectors 204 of electronics module 202, the data being digitized, formatted, and transmitted by integrated circuit 212 to near-field radio exciter/receiver unit 140 or other external electronics 220 like a smartphone. The data is essentially Dynamic Contrast Enhanced Optical Sensing (DCEOS) data. In DCEOS, a dye is introduced into the patient, taken up by the vasculature and delivered to tissue. By measuring the dye-specific change in absorption over time, the blood flow in a tissue of interest is quantified.

In an alternative embodiment requiring less power in the electronics module 202, instead of illuminating the damaged bone with fluorescent illuminators 208, 210, an external fluorescent stimulus light 102 is used at high intensity to provide stimulus light to the ICG, the stimulus light penetrating through skin and tissue to the bone.

Figure 11:
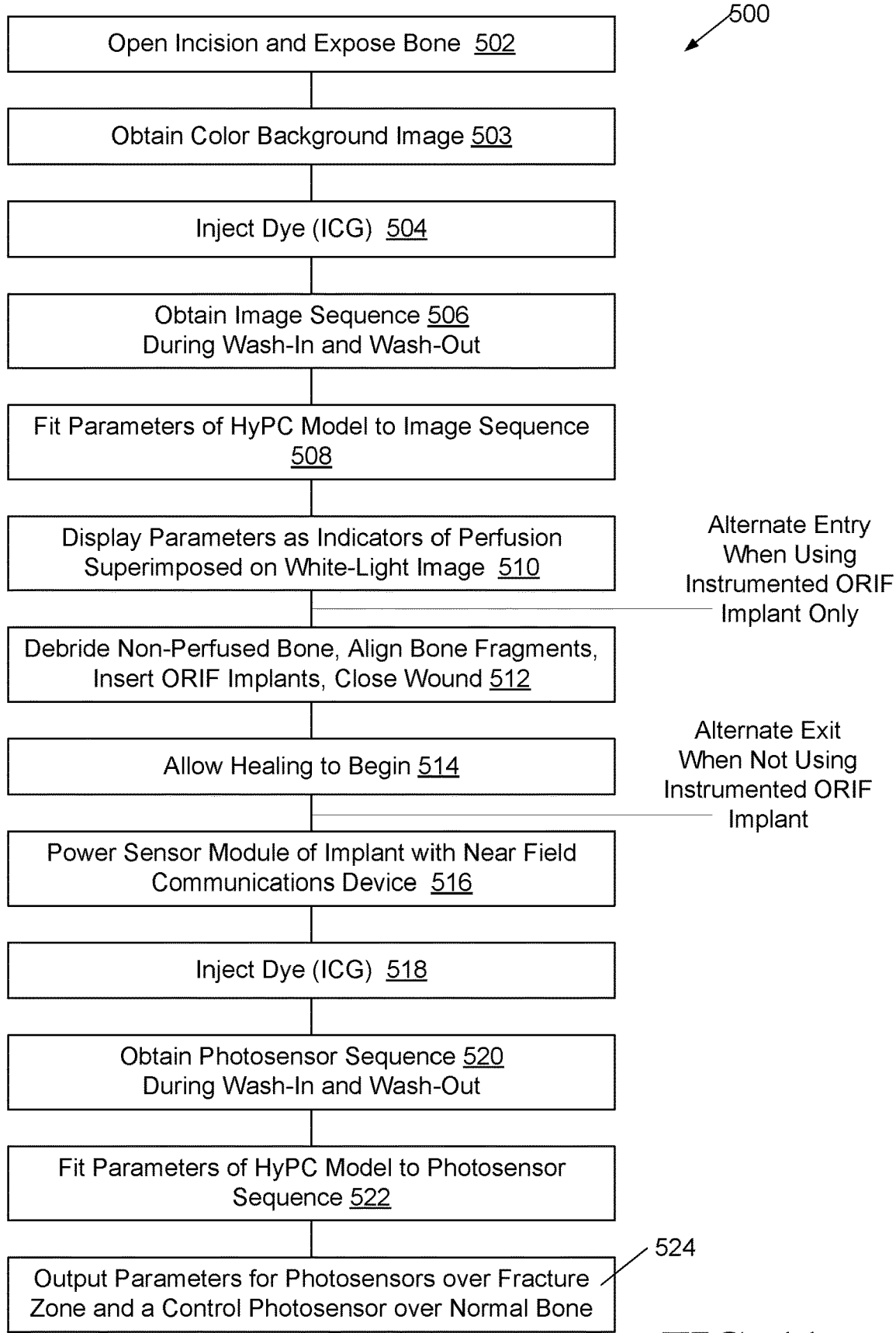
FIG. 11 is a flowchart illustrating an alternative embodiment of a method of evaluating perfusion of bone during and after ORIF surgery where dynamic changes in absorption of light by an injected dye is observed instead of fluorescence by the dye.

In an alternative embodiment, absorption by the dye is measured, instead of fluorescence by the dye; the dye having light absorption characteristics significantly different from that of the heme group common to hemoglobin and myoglobin to permit discrimination by color from the heme found in most tissues during surgery. For example, ICG is a green dye with absorption characteristics differing from heme. The surgical reduction site is opened and the damaged bone is exposed 502 (FIG. 11) A background image is then taken 503, after which the dye, which may be ICG, is injected 504 into the subject. An arterial input function (AIF) is determined using a sensor that detects the dye injection while a sequence of images is obtained 506 during wash-in and wash-out of the fluorescent dye into and from the bone, in embodiments this sequence of images is a video. The sequence of images is captured in a digital image processor, the digital image processor first subtracts the background image from each image in the sequence of images, then fits 508 parameters of the HyPC model to pixels of the sequence of images sequence; the fitted model parameters are displayed 510 as a false-color image that may, should a user desire, be superimposed on a white-light image of the surgical wound and fractured bone. Debridement of the wound is completed, the fracture reduced 512, and one or more ORIF implants inserted, and the wound closed. In some embodiments, the ORIF implant used includes a near-field sensor module. Healing of wound and fracture is allowed 514 to begin. Post-surgery, when it is desired to evaluate perfusion in the fracture zone lying beneath at least one photosensor of the ORIF implant, the sensor module of the implant is powered 516 with a near-field communications device. A background light intensity reading at the photosensor of the implant is obtained. The dye is injected 518, and an arterial input function is obtained. A sequence of photosensor readings is obtained 520 by the sensor module of the ORIF implant and transferred to a processor. The processor then fits 522 parameters of the HyPC model to determine perfusion of bone in the fracture zone. The fitted parameters are then output 524 to permit a user to determine perfusion in the fracture zone.

HyPC Model the HyPC model considers the fast (sometimes called vascular or capillary) component and the slow (sometimes called tissue or parynchema) component of blood in the bone to be separate compartments with separate inputs. In the capillary (fast) phase, the dye does not extravasate from the intravascular space, and variations in arrival time of dye are due completely to the distribution of transit times attributed to the variety of paths available in the "mesh" of capillaries. During the parenchyma (slow) phase, there is exchange between the intravascular and extravascular extracellular space, modeled by an exponential function (first order rate equation). Normally, models such as the AATH assume a single vascular-tissue unit with a single ingress and egress. However, bone is unique in that it has two vascular 'units' supplying a unit of bone cortex, periosteal vasculature and endosteal vasculature. Therefore, the hybrid plug-compartment model models these units separately, treating the first (periosteal) as a plug and the second (endosteal) as a simple two compartment tissue. Our clinical and preclinical experience strongly suggests the separation of arrival times of these two components can differ widely in both normal and pathological conditions, making this 'free' parameter essential to a good fit across all expected cases. While this plug/compartment dichotomy is a simplification of the physiology, it is a reasonable trade-off to limit the degrees of freedom in the model, in order to avoid overfitting the measured data. In contrast to simply using an established model like the AATH model, which would be even less physiologically relevant, the HyPC model provides variables with clinical relevance, such as EBF or PBF, even in cases where the arrival time of the endosteal component is delayed by more than 10 seconds. Preliminary results demonstrate this model can detect modifications in bone perfusion better than using Imax, which can be estimated directly from the images.

In an embodiment, parameters of a bone-specific hybrid plug-compartment (HyPC) kinetic hemodynamic model are fit to data originating either in the ORIF implant or the fluorescent imaging camera. Extracted parameters at individual pixels of the imaging camera stream of the bone in the open surgical site are displayed as a false-color image superimposable on a three-color white-light image of the open surgical site, these images indicate blood flow to the bone. Extracted parameters from the individual photosensors of the ORIF implant are presented to the user as an indication of blood flow to the damaged bone.

Theory

The time-dependent concentration of dye in a tissue, $Q(\vec{r},t)$, at some position, $\vec{r}$, following a bolus injection is given by the convolution theory of tracer kinetics:

$$Q(\vec{r},t) = C_a(t) * F(\vec{r}) R(\vec{r},t), \qquad (1)$$

where $C_a(t)$ is the time-dependent concentration of dye in the arterial system, $F(\vec{r})$ is the blood flow at position, $\vec{r}$, and $R(\vec{r},t)$ is the impulse residue function (IRF) at position, $\vec{r}$. The IRF is defined as the fraction of dye remaining in the tissue at time, t, following an ideal bolus injection approximating a delta function. In the language of linear time-invariant systems, R(t) represents a 'transfer function' mapping $C_a(t)$ to $Q(t)$.

If at position, $\vec{r}$, there exists multiple quasi-independent vascular systems (locally independent with separate feeding arteries), then a "bulk" FR(t) can be defined as the superposition of the FR(t) functions from each capillary unit. Most indicator-dilution applications are found in 3D medical imaging (e.g., MRI, CT) and therefore, a voxel covers a single vascular unit. If that vascular unit communicates with other interconnected compartments of tissue, a compartment model is used. Otherwise, if the dye remains in the intravascular space (IVS), a single compartment model is considered, but may include parameter(s) to describe the distribution of capillary transit times.

Compact bone is supplied by the periosteal and endosteal blood vessels. The periosteal vessels insert into the periosteum, a connective tissue that surrounds the bone. These vessels travel into the superficial compact bone providing blood flow from the exterior. The endosteal blood supply consists of the large nutrient vessels that insert through holes in the bone and run along the inside of the bone, branching off into central and perforating canals, and supplying blood from the interior to the inner two-thirds of the cortex as well as the medullary cavity; the medullary cavity also contains the bone marrow, and porous blood vessels running through the marrow allow for new blood cells to enter the circulatory system.

When imaging volume units are large enough, such as in planar fluorescence imagining where light penetrates 1-2 cm of cortical bone, a bulk FR(t) will be comprised of these two bifurcated periosteal and endosteal systems. To this end, we describe a novel, bone-specific kinetic model representing the superposition of a plug flow model (periosteal) and a two-compartment model (endosteal) with independent bolus arrival times, which we assign the name "hybrid plug/compartment" model, or "HyPC" for short.

Figure 6A:
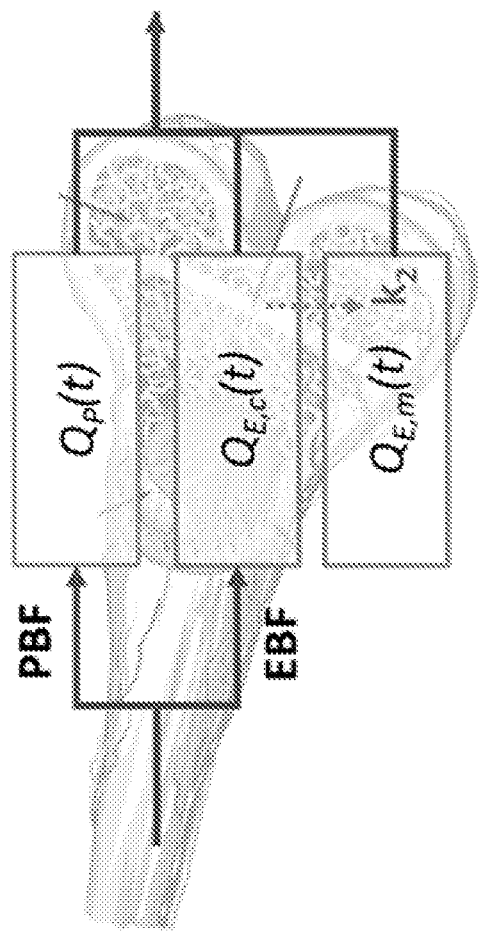
FIGS. 6A-6B.
Figure 6B:
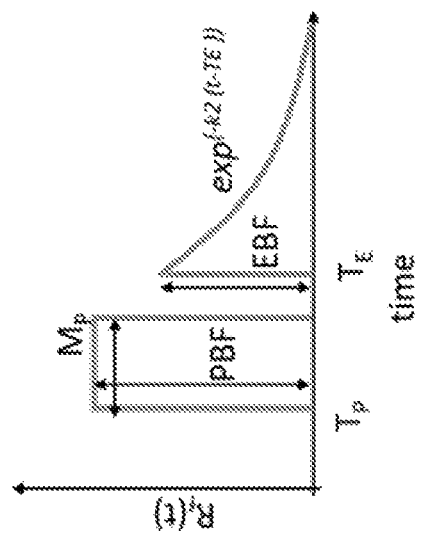

Let there be two distinct tissue compartments, periosteal (P) and endosteal (E) that have a time-dependent tissue concentration of dye, $Q_P(t)$ and $Q_E(t)$, respectively, as illustrated in FIG. 6A. Within the HyPC model, $Q(\vec{r},t)$ representing the region of interrogation at $\vec{r}$, can be considered a summation of partial volumes of $Q_P(t)$ and $Q_E(t)$, such that:

$$Q(\vec{r},t) = d_P(\vec{r})Q_P(\vec{r},t) + d_E(\vec{r})Q_E(\vec{r},t) \quad (2)$$

where $d_P(\vec{r})$ and $d_E(\vec{r})$ are the fractional volumes interrogated by light when positioned at r, and the convolution $$Q(\vec{r},t) = [d_P(\vec{r})iPBF(\vec{r})R_P(\vec{r},t) + d_E(\vec{r})iEBF(\vec{r})R_E(\vec{r},t)] * C_a(t) \quad (3)$$

where iPBF and iEBF are the instrument-independent periosteal blood flow and quantitative endosteal blood flow (the actual physiologic blood flow in these regions independent of the type of instrument used to measure them). In practice, it is not always possible to determine the dP and dE. Therefore, we simplify from Eq. 2 to PBF and EBF, the periosteal and endosteal blood flows for a specific imaging geometry and assumed partial volume distribution. The aggregate FR(t) describing the sum of flow-scaled R(t)s in the periosteum and endosteum is defined as $$FR(\vec{r},t) = [PBF(\vec{r})R_P(\vec{r},t) + EBF(\vec{r})R_E(\vec{r},t)] \quad (4)$$

For subjects with similar age and bone density, the iPBF will correlate with PBF, and iEBF will correlate with EBF.

The IRFs $R_P(r,t)$ and $R_E(r,t)$ are defined as:

$$R_P(\vec{r},t) = \begin{cases} 0 & \text{for } t < TP(\vec{r}) \\ 1 & \text{for } TP(\vec{r}) < t < TP(\vec{r}) + MP(\vec{r}) \\ 0 & \text{for } t > TP(\vec{r}) + MP(\vec{r}) \end{cases} \quad (5.1)$$

$$R_E(\vec{r},t) = \begin{cases} 0 & \text{for } t < TE(\vec{r}) \\ e^{-k_2(\vec{r})(t - TE(\vec{r}))} & \text{for } t > TE(\vec{r}) \end{cases} \quad (5.2)$$

where $TP(\vec{r})$ is the arrival time of the bolus to the periosteal vasculature centered under $\vec{r}$, $MP(\vec{r})$ is the minimum time required for dye to travel across the periosteal vasculature, and $TE(\vec{r})$ is the arrival time of the bolus to the endosteal vasculature in the area of interrogation. Therefore, there are six parameters that are recovered by applying the HyPC model: $PBF(\vec{r})$, $EBF(\vec{r})$, $TP(\vec{r})$, $MP(\vec{r})$, $TE(\vec{r})$, $-k_2(\vec{r})$. Furthermore, we define the following calculated parameters: total bone blood flow, TBF=PBF+EBF; and EBF fractional flow, EFF=EBF/TBF.

Animal Experiment and Fluorescence Acquisition

A single pig was used a proof-of-concept. The pig was sedated and placed under general anesthesia using isoflurane. Peripheral veins were catheterized for administration of ICG. Once a deep plane of anesthesia was confirmed, the leg was surgically opened to expose the intact periosteum. A large artery, such as the superficial femoral artery, was blunt dissected and a piece of black cloth was placed between it and the leg to allow direct arterial input function (AIF) characterization. Imaging was performed at baseline and after each of the following surgical manipulations: traverse tibial osteotomy at two locations, removal of proximal periosteum, and removal of distal periosteum. Imaging was performed using the Zeiss Pentero OPMI 800 operating in FLOW800 mode at a working distance of 300 mm. Infrared video was recorded to capture the injection of ICG, and its wash-in and wash-out of the tissue of interest.

Imaging Data Analysis

The videos were transferred to a PC and loaded into MATLAB (TheMathWorks, Warrick, MA) and analyzed using an in-house developed implementation of the HyPC model. First videos were processed using the VideoReader function into a time series of images saved in a single array. Using the imfreehand tool, the region corresponding to the exposed artery was selected and saved as the AIF, $C_a(t)$. The same tool was used to select regions-of-interest (ROIs) along the length of the bone. Each ROI was then fit with the HyPC model using a two-step approach to minimize the chance of overfitting. First, the initial wash-in slope (25% past the time of peak intensity) of the curve was fit using a plug-flow only model, to estimate PBF, TP and MP. These parameters were then used as priors for the plug component of the full model, which was fit to the whole curve to recover EBF, TE and $k_2$. For both fitting procedures, fminsearchbnd was used. When applied on a pixel-by-pixel basis to produce parametric maps, the image stack was first median filtered with a 4×4 pixel window using medfilt2, and then reduced in size by ¼. This was done to improve the signal-to-noise and reduce the time required to compute the maps.

To validate the recovered FR(t) function, a model-independent deconvolution was performed using the truncated SVD approach. While FR(t) recovered this way will have oscillations expected with an SVD approach, if the HyPC model accurately represents the true FR(t), it should show agreement with the SVD function averaged over time.

Results

Figure 7A:
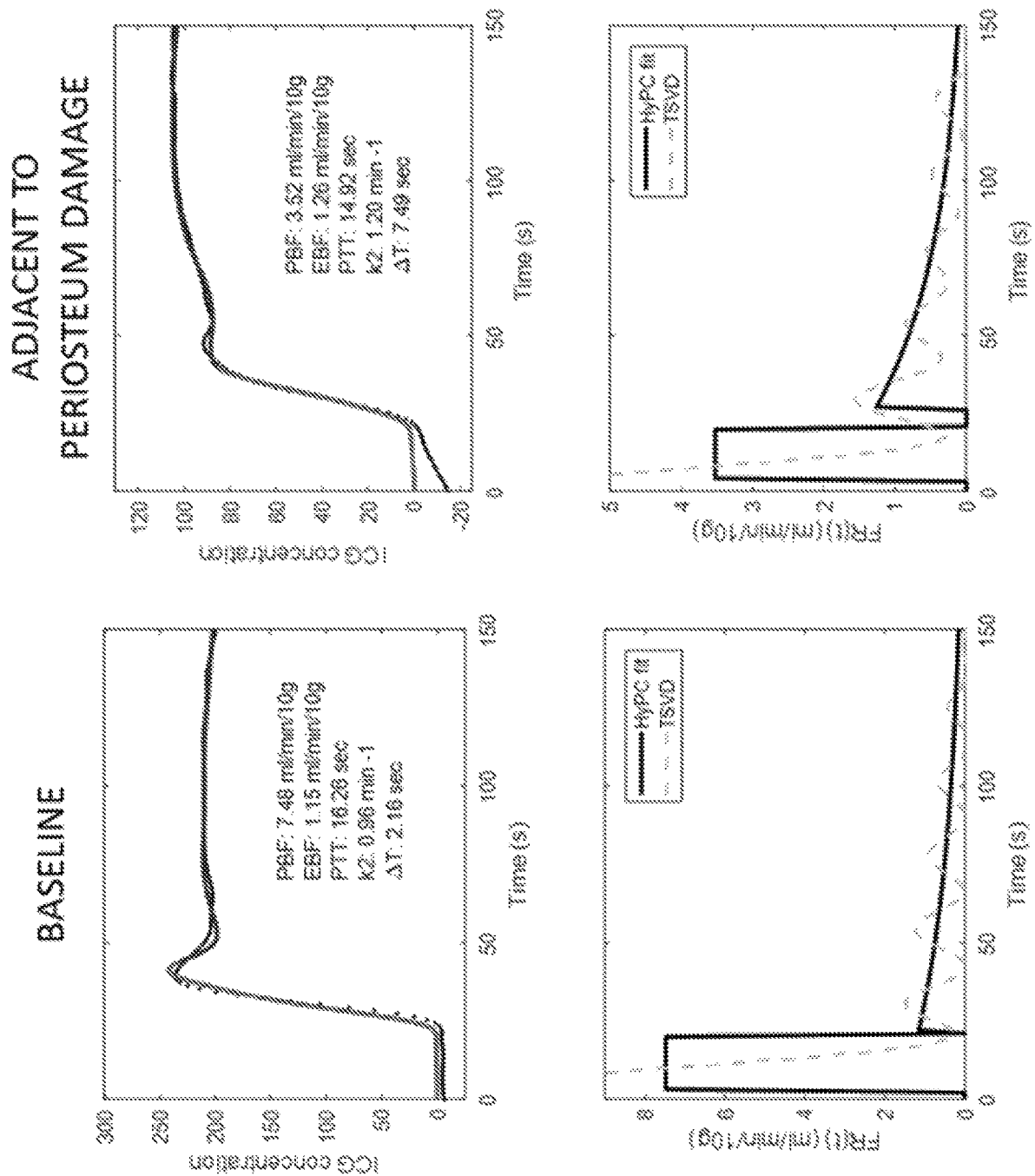
FIG. 7A-7B. Top Row. ICG intensity (black dots) measured during baseline, after endosteal flow is disrupted and after both endosteal and periosteal flow is disrupted. Curve fitting is performed in two steps: first, a plug flow model is fit to the initial slope (red line) then the entire curve is fit using the hybrid plug and compartment (HyPC) model (blue line). Bottom Row. The recovered flow-scaled impulse response functions, FR(t), corresponding to the curves in the top row are shown (solid lines). For comparison, FR(t) estimated using Tikhonov deconvolution also shown (dashed lines).
Figure 7B:
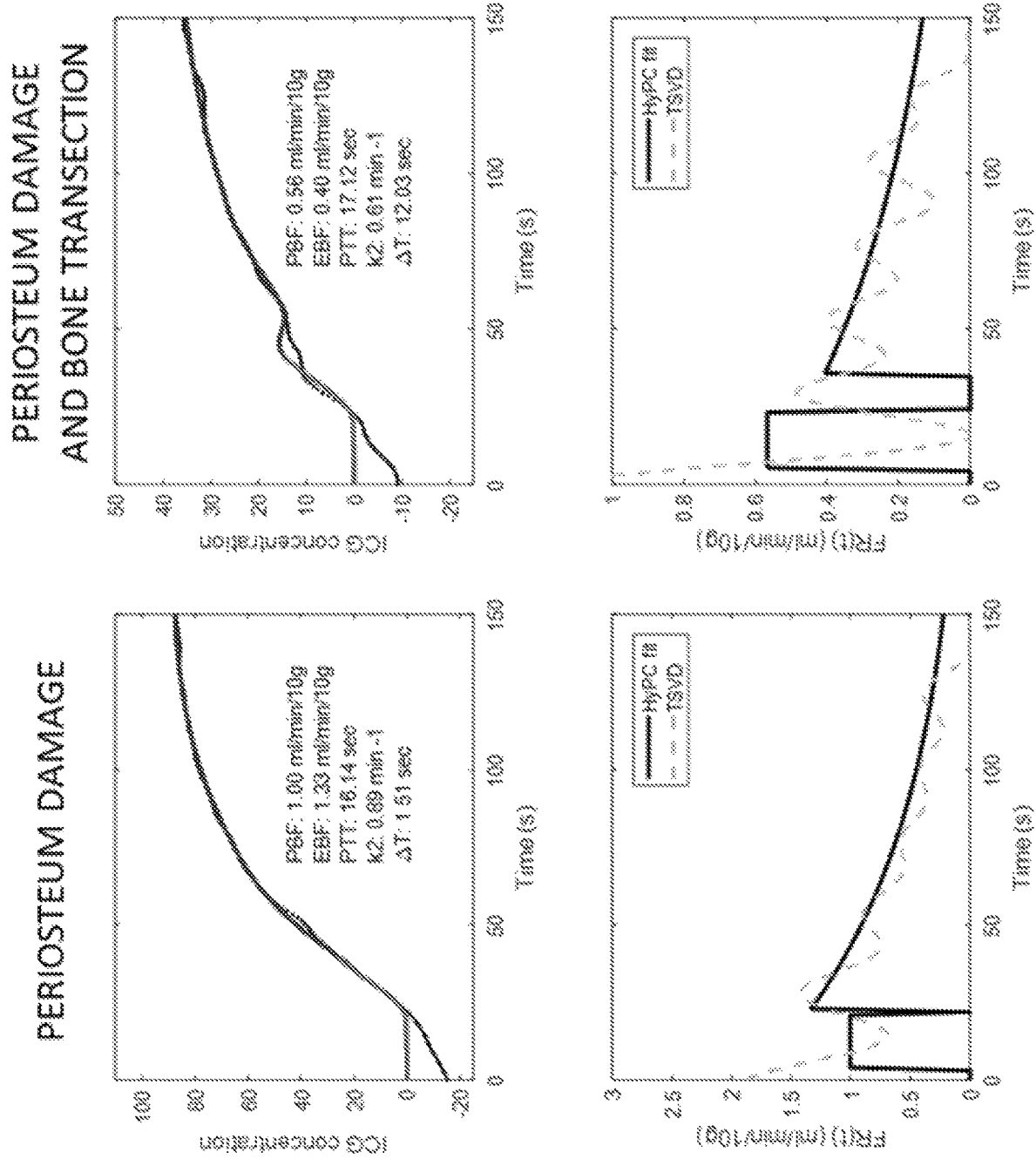

FIG. 7A-B shows the results of the two-step fit of HyPC to the ICG curves extracted from ROI analysis. For each curve, the recovered values for periosteal blood flow (PBF) and endosteal blood flow (EBF), and calculated total bone blood flow (TBF) and endosteal flow fraction (EFF) are shown. Periosteal damage results in marked decrease in PBF from baseline (7.48 ml/min/100 g of bone). The ROI adjacent to damaged periosteum decreased in PBF by 52.9%, and the ROI at the site of damage decreased by 86.7%. The endosteal flow remained more or less constant, between 1.15 and 1.33 ml/min/100 g of bone; transection of the bone in two locations further reduced the PBF by 40% and reduced the EBF by 70%. The recovered flow-scaled IRFs show the degree to which the relative levels of BF compared to total blood flow (TBF) increased during the evolution of injury. With a baseline of 12.8%, EFF increased to 56.5% after periosteal damage, and remained at 40% following transection of the bone.

The nonparametric IRFs recovered using truncated SVD (TSVD) show good agreement with the HyPC fit recovered FR(t) functions (FIG. 7A-7B; bottom row). While the dramatic oscillations are a feature of this type of highly unstable deconvolution, nevertheless, the center of these oscillations tracks very closely the HyPC FR(t), suggesting that the kinetic model is valid.

Figure 8:
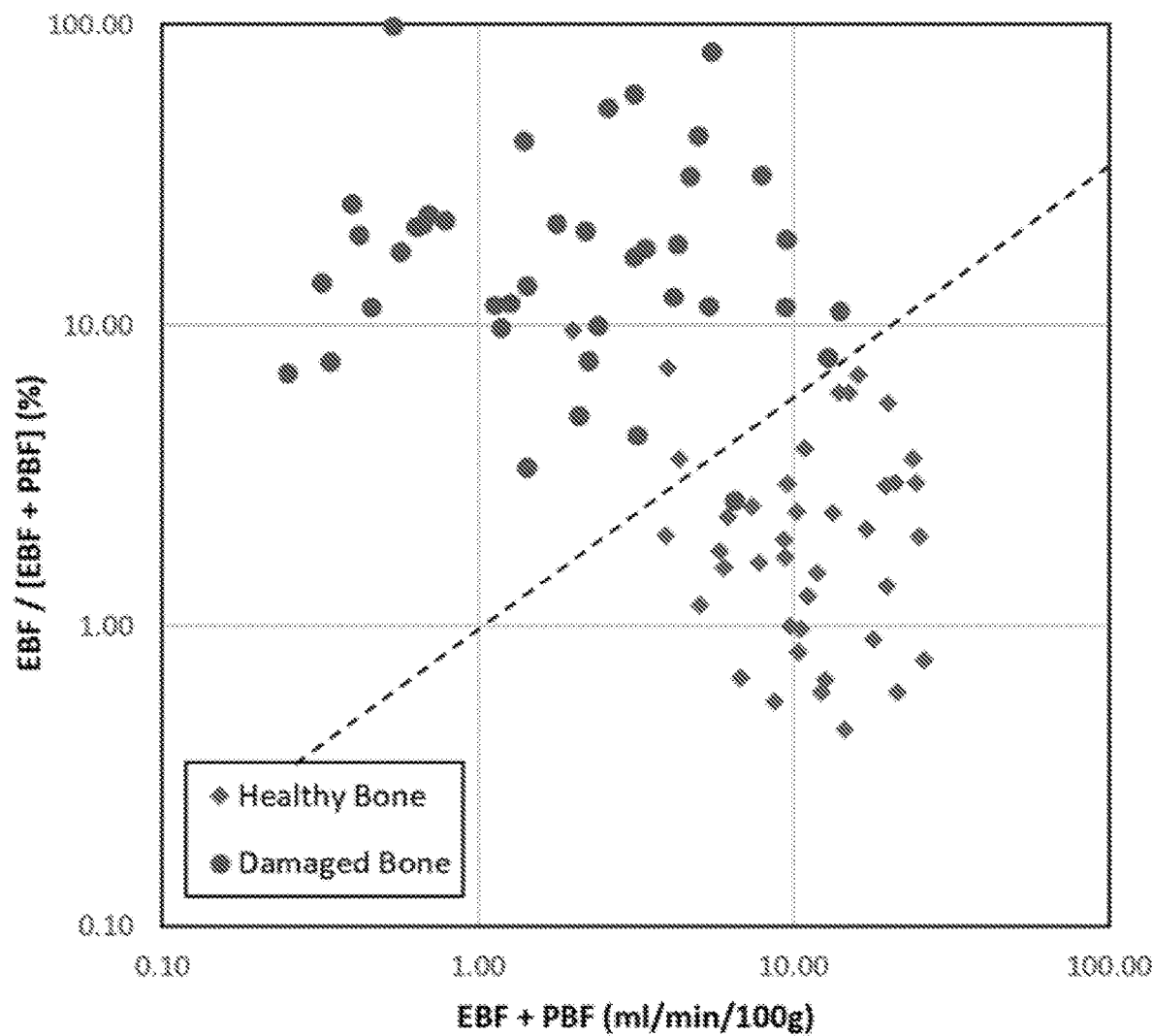
FIG. 8. Is a graph illustrating SVM classification of healthy and damaged bone according to total blood flow (TBF, TBF=endosteal blood flow (EBF)+periosteal blood flow (PBF)) and EBF as percent of total flow (%). As shown, damage to bone causes a decrease in TBF and increase in fraction of PBF, generally, though not always both at once. Data is from 4 pigs using 84 data points.

In addition to ROI analysis, the HyPC model is effective at producing parametric maps. Using the procedure described previously, parametric maps of TBF and EFF were calculated and are shown in FIG. 8. For efficiency, the method allows identification of an area of interest and calculates the values for those pixels first before populating the rest of the field of view in random order, accounting for the speckled appearance of the adjacent tissue.

DISCUSSION

While existing techniques in MRI and PET have been explored to quantify bone blood flow, we present the first bone-specific kinetic model that considers the unique interrogation volume of fluorescence imaging systems. Since the signal is acquired from both superficial tissue and tissue 1-1.5 cm below the surface of the bone, changes in ICG fluorescence intensity over time will reflect the different wash-in and washout dynamics of the periosteal and endosteal blood supply. It was hypothesized that an appropriate model would need to exhibit the following criteria:
1) the difference in arrival times of dye in the periosteum and endosteal compartment, and
2) the porous nature of endosteal vessels which freely exchange material with the medullary cavity of the bone.

The proposed HyPC model is related to the adiabatic approximation to the tissue homogeneity (AATH) model, which fulfills criterion #2, but HyPC is modified to decouple the fast and slow phase components, allowing for criterion #1.

A few of the recovered FR(t) functions in FIGS. 7A & 7B demonstrate the improved utility of this model compared with previous single input models like AATH and GCTT; in one case, the EBF was higher than the PBF, and in another, there was a gap between the exit of the dye in the periosteum and the arrival of the dye in the endosteum. Neither of these two scenarios would be allowed by previous models, or by a constrained nonparametric deconvolution. The close tracking of the nonparametric deconvolution suggest the HyPC model is reasonably valid. Parametric maps of TBF and EFB fraction in FIG. 8 clearly show the marked changes expected in bone flow following such disturbances. Total blood flow at baseline was about 10 ml/min/100 g. Following osteotomy, TBF decreased markedly between transverse cuts due to the elimination of both endosteal and periosteal flow; distal to the cuts TBF was reduced mainly due to a disturbance in periosteal flow, suggesting transection of a supplying periosteal vessel. However, the endosteal flow remained intact. Subsequent stripping of the periosteum caused a reduction in TBF across the whole site, to levels around 3 ml/min/100 g, and revealed the reduction in endosteal flow proximal to the transection.

There are some limitations to this study that will be addressed in future work: First, the current method of obtaining the AIF is not practical in the clinical setting, and a pulse dye densitometer would be better-suited to this purpose. Second, fluorescence should be corrected by the optical properties of the tissue for within-patient and between-patient comparisons. Additionally, using FEM to estimate the sensitivity to the periosteal and endosteal regions would improve quantitation. Notwithstanding these limitations, HyPC kinetic imaging could help surgeons evaluate the endosteal and periosteal supply during surgery, enabling discrimination between viable and non-viable tissue during debridement—an improvement which could reduce infection and non-union rates. Furthermore, the ability to directly quantify endosteal and periosteal blood flow may help the surgeon decide between an intramedullary nail or plate and screw fixation.

Human Trial

Figure 9:
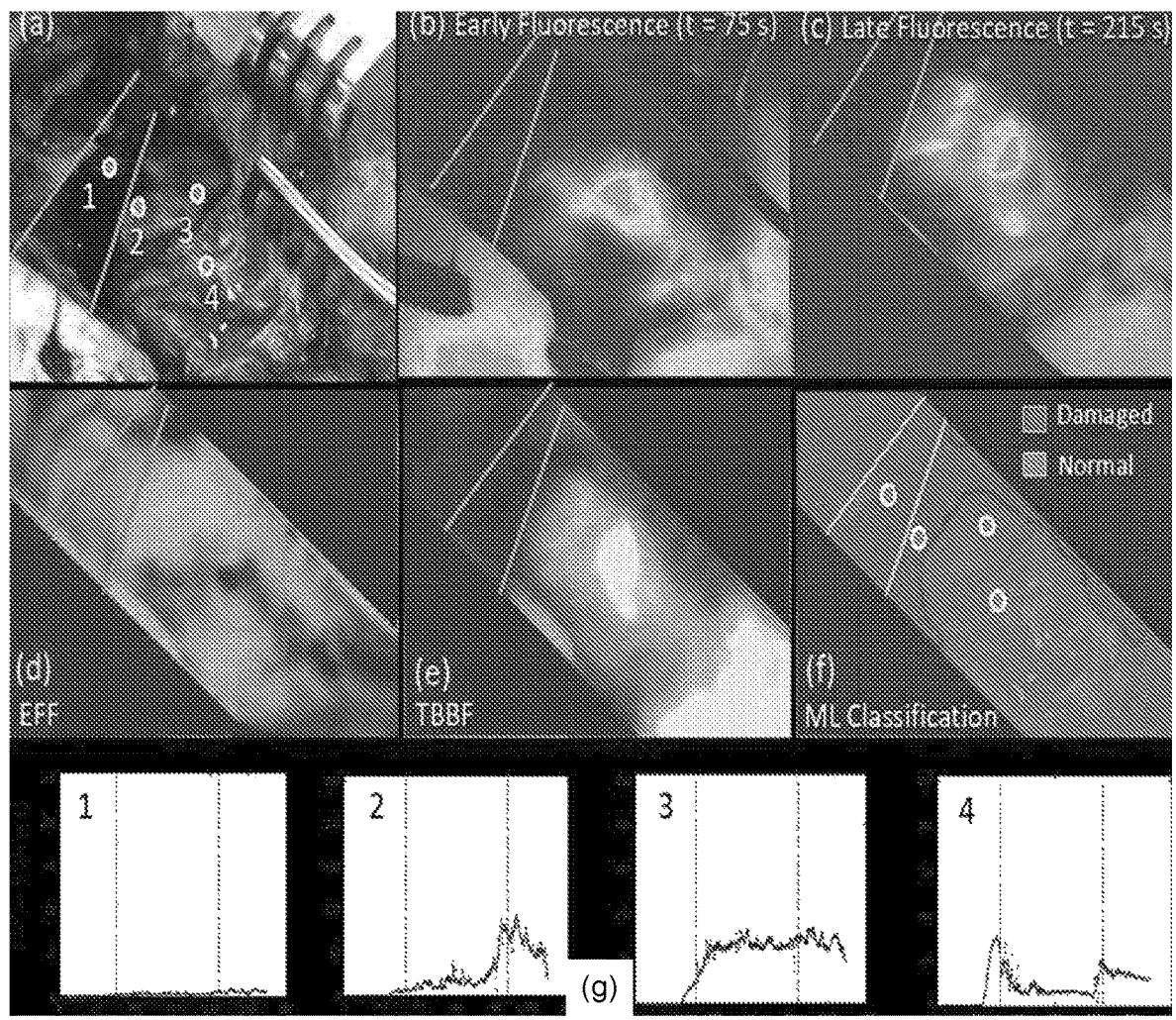
FIG. 9 is a sequence of data and images recorded during open reduction surgery of a human patient with a Gustilo type 3C open tibia fracture showing good quantification of perfusion.

Eight human patients during orthopedic surgeries were examined with a prototype apparatus resembling that of FIG. 1. This examination demonstrated that dynamic ICG-based fluorescent analysis can assess bone perfusion during surgery. Fluorescence images were recorded every 0.267 seconds for 4.5 minutes. Following 20 seconds of pre-injection imaging, 0.1 mg/kg of ICG was administered intravenously to the patient. After fluorescent images were acquired, a white-light image was taken. FIG. 9 summarizes the ICG based dynamic data we acquired from this patient. In FIG. 9 ROIs #1 was fracture, #2 was closest to the fracture/segmental bone defect and ROIs #3 and #4 are more proximal from the fracture/segmental bone defect. The more proximal ROIs (#3 and #4 in FIG. 9(a)) were, as expected, better perfused than that of the ROIs in or close to the fracture site, which is evinced by the brighter regions in the fluorescence intensity images at 75 and 215 secs. (FIG. 9(b)&(c)), and earlier wash-in dynamics indicating patency in the endosteal supply (FIG. 9(g)). This trend is further reflected in EFF (FIG. 9(d)) and TBBF (FIG. 9(e)) where more proximal ROIs demonstrate brighter signal than more distal ROIs. FIG. 9(f) demonstrates, use of machine learning classification to establish a boundary between healthy and damaged bone based off the TBBF and EFF (%) values, which were the variables that performed best in the porcine preclinical model. In this study, a similar approach will be taken in that we will evaluate all ICG-based HyPC derived variables (simple kinetic curve-derived variables as well as modelling-derived variables) to select the variable or combination of variables that most effectively predicts unplanned reoperation and infection. This will then be used to establish boundaries using these machine learning techniques.

Alternatives

In an alternate embodiment, we propose using machine learning to classify the dye concentration curves. This approach uses deep learning by transforming the curves to images and training a convolutional neural network (CNN) to classify the images according to healthy and damaged bone.

In another alternate embodiment, we propose other preexisting kinetic models to approximate the underlying kinetics of the bone. In one alternative embodiment, the model used is an adiabatic approximation to the tissue homogeneity (AATH) model, in other alternative embodiments the model is a simple kinetic model such as maximum fluorescence or time-to-peak.

The teachings herein have been reduced to practice by fitting both simulated and real experimental data acquired on a pig bone fracture model and on a human subject. For the animal data, optical signal was acquired during ICG injection and washout, along the length of the bone before and after bone injury. Marked differences between the intact and injured bone (both by stripping the bone and transversely cutting the bone) were seen. In another experiment, five pigs were subjected to fractures of the femur, including transection of the bone and stripping of the periosteum. Total Blood Flow (TBF) (Periosteal Blood Flow (PBF)+Endosteal Blood Flow (EBF)) and the relative fraction of EBF to TBF (also called "slow flow fraction" %) of regions with soft tissue or bone damage were compared with healthy tissue. A clear decision boundary emerged which demonstrates the diagnostic or predictive potential of these measurements.

A requirement of tracer-kinetic methodology is the use of a contrast dye. In one embodiment, indocyanine green (ICG) is used because it is FDA-approved and readily available. I.V. injection of ICG would therefore be required. In the context of surgery and post-surgical recovery, I.V. access is standard of care and is not a significant problem. For long-term follow up, it may be overcome by different route of administration (e.g., oral). In alternative embodiments, other non-specific dyes such as: methylene blue, fluorescein sodium; non-FDA approved dyes like IRDye700 and IRDye800 could be FDA approved in the future and would be suitable.

Figure 10:
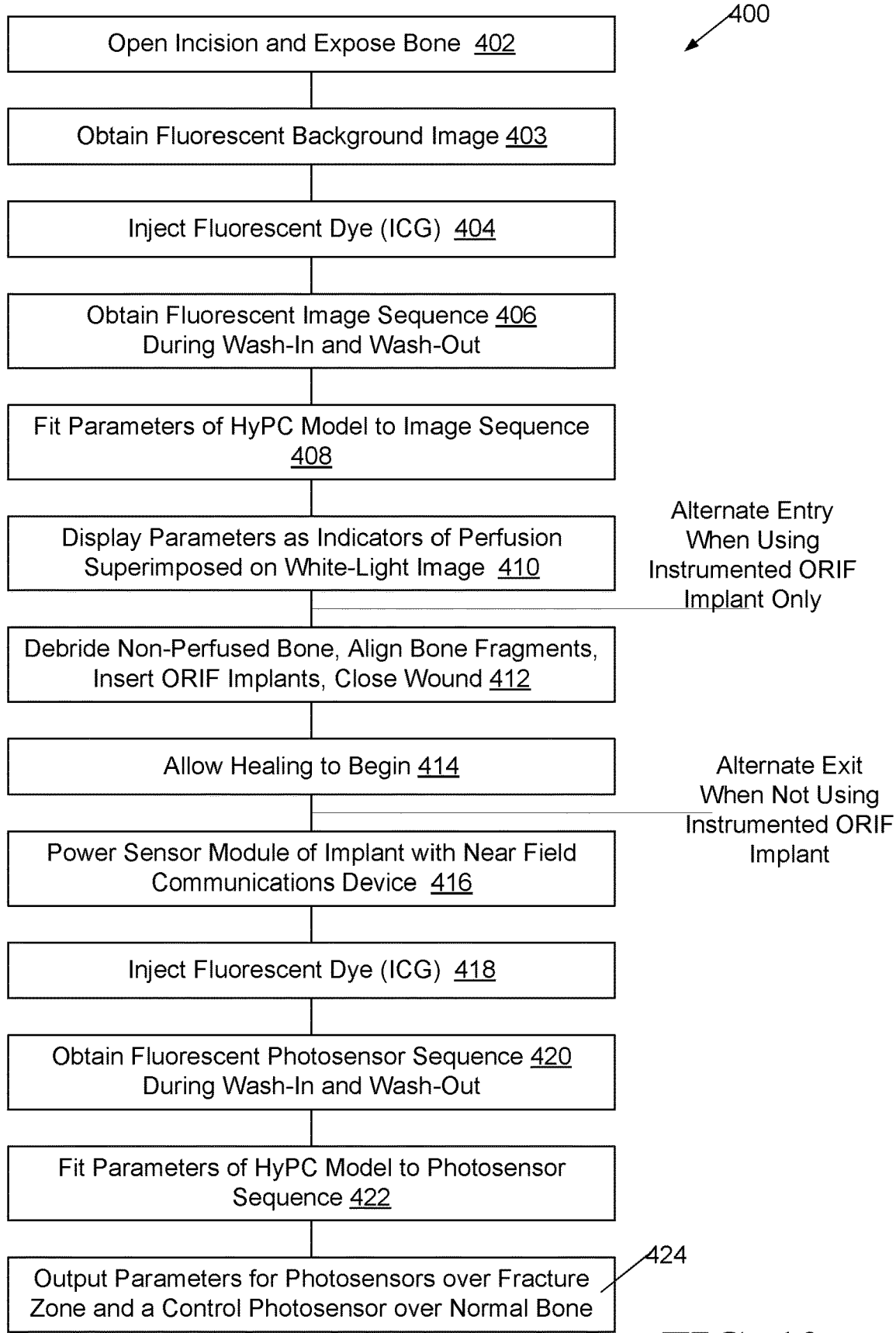
FIG. 10 is a flowchart illustrating an embodiment of a method of evaluating perfusion of bone during and after ORIF surgery.

In an embodiment, the apparatus descried herein is operated according to a method 400 illustrated in FIG. 10. The method includes beginning ORIF surgery by making an incision and exposing 402 the subject's fractured bone. Fluorescent imaging stimulus-wavelength illumination is applied with a fluorescent emissions wavelength camera positioned to image the surgical wound and the fractured bone. A fluorescent background image is then taken 403, after which the fluorescent dye, which may be ICG, is injected 404 into the subject. An arterial input function (AIF) is determined using a sensor that detects the ICG injection while a sequence of images is obtained 406 during wash-in and wash-out of the fluorescent dye into and from the bone, in embodiments this sequence of images is a video. The sequence of images is captured in a digital image processor, the digital image processor first subtracts the fluorescent background image from each image in the sequence of images, then fits 408 parameters of the HyPC model to pixels of the sequence of images; the fitted model parameters are displayed 410 as a false-color image that may, should a user desire, be superimposed on a white-light image of the surgical wound and fractured bone. The user—typically a surgeon—then completes debridement of the wound, reduces 412 the fracture, installs one or more ORIF implants such as a plate screwed to each major fragment of the fractured bone, and closes the wound. In some embodiments, the ORIF implant used includes a near-field sensor module. Healing of wound and fracture is allowed 414 to begin.

In an alternative embodiment, imaging the bone during surgery is omitted but the ORIF implant used includes the near-field sensor module. In another alternative embodiment, the near-field sensor module is omitted and the subject receives standard postoperative care. In another alternative embodiment, the bolus of dye is administered through a route, such as orally or intranasally, that is different from the intravenous injection route specified above.

Post-surgery, when it is desired to evaluate perfusion in the fracture zone lying beneath at least one photosensor of the ORIF implant, the sensor module of the implant is powered 416 with a near-field communications device. A background fluorescence reading is obtained. The fluorescent dye is injected 418, which in an embodiment is ICG, and an arterial input function is obtained. A sequence of photosensor readings is obtained 420 by the sensor module of the ORIF implant and transferred to an image processor. The image processor then fits 422 parameters of the HyPC model given above to determine perfusion of bone in the fracture zone. The parameters are then output to permit a user to determine perfusion in the fracture zone.

In another embodiment, an after-debridement, pre-insertion of ORIF implant, bone perfusion image is obtained using the method of FIG. 10 for many subjects, together with fracture classification and post-surgical follow-up reports of infections, disunion, and other complications. A classifier is then trained on the images and follow-up reports to provide indications of when additional debridement is recommended before closing the surgical wounds.

A positive impact on outcome would make this disclosure the standard-of-care ORIF. For example, approximately 188,900 surgeries were performed in 2012 in the US to treat fracture or dislocation of lower extremity. A high number of fractures that are complex with penetrating wounds and soft tissue damage are prone to infection. About 60% of open bone fractures results in infection, and these infections substantially increase the cost, morbidity and potential for limb loss. These are strong justifications for preventative measures to reduce the risk of infection, including imaging during the time of surgery for optimal bone debridement and then using fixation hardware with imbedded optics to allow early monitoring and detection of infection. The kinetic model could be used in an open surgery imaging context, where a device like the Stryker Spy Elite could be used to map endosteal and periosteal blood flow, and this could be licensed as a software package.

Combinations

The system, method, features, and concepts described herein may be combined in multiple ways. Among combinations anticipated by the inventors are:

An implant designated A for open surgical reduction with internal fixation of fractures, the implant comprising a rigid plate or rod and an integrated electronics module; the integrated electronics module including at least two optical sensors adapted to sense fluorescent emissions, at least one fluorescent stimulus wavelength light, and a near-field digital radio; the optical sensors coupled through at least one analog to digital converter to the near-field digital radio.

An implant designated AA including the implant designated A wherein the rigid plate or rod of the implant comprises polyethylene terephthalate glycol-modified (PETG) or ultra-high molecular weight polyethylene (UHMWPE).

A system designated AB including the implant designated A or AA and a near-field radio exciter-reader adapted to power and receive data from the implant, a processor, and a memory coupled to the processor; where the processor is configured by machine readable code in the memory to obtain a sequence of readings of the optical sensors from the implant and to fit the sequence of readings to a model of perfusion of bone.

A system designated AC including the system designated AB where the model of perfusion of bone is a bone-specific kinetic model comprising a superposition of a plug flow model to model periosteal perfusion and a two-compartment model to model endosteal perfusion.

A system designated AD including the system designated AC where the plug flow model and two-compartment model have independent bolus arrival times.

A system designated B, either stand-alone or including the system designated AD, AC, or AB, for use during surgery for open reduction and internal fixation of fractures comprising at least one light configured to stimulate fluorescent emissions from a fluorescent dye, an injector adapted to inject the fluorescent dye into a subject, a camera configured to provide a sequence of images of fluorescent emissions from the fluorescent dye to an image processor, the image processor being configured by machine readable code in the memory to fit the sequence of images to a model of perfusion of bone.

A system designated BA including the system designated B where the model of perfusion of bone is a bone-specific kinetic model comprising a superposition of a plug flow model to model periosteal perfusion and a two-compartment model to model endosteal perfusion.

A method designated C including applying fluorescent stimulus-wavelength illumination to a surgical wound exposing a fractured bone of a subject; imaging the surgical wound and the fractured bone with a fluorescent emissions wavelength camera positioned to image the surgical wound and the fractured bone to provide a sequence of fluorescent emissions images; injecting a fluorescent dye into the subject, the sequence of fluorescent emissions images comprising images of wash-in and wash-out of the fluorescent dye; determining an arterial input function (AIF) using a sensor that detects the fluorescent dye; capturing the sequence of fluorescent emissions images in a digital image processor; and fitting parameters of a bone-specific kinetic model comprising a plug flow model to model periosteal perfusion and a two-compartment model to model endosteal perfusion to pixels of the sequence of fluorescent emissions images.

A method designated CA including the method designated C where the fluorescent dye is indocyanine green.

A method designated D either stand-alone or including the method designated C or CA, and further including implanting an open reduction and internal fixation (ORIF) implant onto a fractured bone of a subject, the ORIF implant comprising an electronics module; allowing the fracture to begin healing; using a near-field radio, causing the electronics module to emit fluorescent stimulus-wavelength illumination into a fracture zone of the fractured bone; injecting a fluorescent dye into the subject; sensing fluorescence from the fracture zone with a fluorescent emissions wavelength photosensor of the electronics module to provide a sequence of fluorescent emissions readings, where the sequence of fluorescent emissions readings comprises readings of wash-in and wash-out of the fluorescent dye; and fitting parameters of a bone-specific kinetic model that models both periosteal perfusion and endosteal perfusion to the sequence of fluorescent emissions readings.

A method designated E includes implanting an open reduction and internal fixation (ORIF) implant onto a fractured bone of a subject, the ORIF implant comprising an electronics module; allowing the fracture to begin healing; using a near-field radio, causing the electronics module to emit illumination into a fracture zone of the fractured bone; injecting a light-absorbing dye into the subject; sensing changes to light absorption in the fracture zone with a photosensor of the electronics module to provide a sequence of light absorption readings, where the sequence light absorption readings comprises readings during wash-in and wash-out of the dye; and fitting parameters of a bone-specific kinetic model that models both periosteal perfusion and endosteal perfusion to the sequence of light-absorption readings.

A method or system designated F including the method designated D, E, CA, or C or the system designated AB, AC, AD, B, or BA, where the bone-specific kinetic model models two tissue compartments, periosteal (P) and endosteal (E), each having a time-dependent tissue concentration of dye, QP(t) and QE(t), respectively; where a region of interrogation is $\vec{r}$, and fitting parameters of the model to observed total concentration of dye versus time fits parameters PBF($\vec{r}$) representing periosteal blood flow, EBF($\vec{r}$) representing endosteal blood flow, TP($\vec{r}$) representing the arrival time of a dye bolus to periosteal vasculature centered under $\vec{r}$, MP($\vec{r}$) representing a minimum time required for dye to travel across the periosteal vasculature, TE($\vec{r}$) representing an arrival time of the dye bolus to the endosteal vasculature in the area of centered under $\vec{r}$, and permits calculation of total bone blood flow, TBF=PBF+EBF; and EBF.

Changes may be made in the above system, methods or device without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A system comprising:
    an open surgical reduction with internal fixation (ORIF) implant for treatment of fractures, the implant comprising:
        a rigid plate or rod and an integrated electronics module,
        the integrated electronics module comprising at least two optical sensors adapted to sense fluorescent emissions, at least one fluorescent stimulus wavelength light source, and a near-field digital radio; the optical sensors coupled through at least one analog to digital converter to the near-field digital radio,
        wherein the rigid plate or rod of the implant comprises polyethylene terephthalate glycol-modified (PETG) or ultra-high molecular weight polyethylene (UHMWPE);
    a near-field radio exciter-reader adapted to power and receive data from the implant, a processor, and a memory coupled to the processor; where the processor is configured by machine readable code in the memory to obtain a sequence of readings of the optical sensors from the implant and to fit the sequence of readings to a model of perfusion of bone.

2. A system comprising:
    an open surgical reduction with internal fixation (ORIF) implant for treatment of fractures, the implant comprising:
        a rigid plate or rod and an integrated electronics module,
        the integrated electronics module comprising at least two optical sensors adapted to sense fluorescent emissions, at least one fluorescent stimulus wavelength light source, and a near-field digital radio; the optical sensors coupled through at least one analog to digital converter to the near-field digital radio, wherein the rigid plate or rod of the implant comprises polyethylene terephthalate glycol-modified (PETG) or ultra-high molecular weight polyethylene (UHMWPE);

a near-field radio exciter-reader adapted to power and receive data from the implant, a processor, and a memory coupled to the processor; where the processor is configured by machine readable code in the memory to obtain a sequence of readings of the optical sensors from the implant and to fit the sequence of readings to a model of perfusion of bone;

where the model of perfusion of bone is a bone-specific kinetic model comprising a superposition of a plug flow model to model periosteal perfusion and a two-compartment model to model endosteal perfusion.

3. The implant of claim 2 wherein the rigid plate or rod of the implant comprises polyethylene terephthalate glycol-modified (PETG).

4. The system of claim 2 where the plug flow model and two-compartment model have independent bolus arrival times.

5. The system of claim 4, where the bone-specific kinetic model models two tissue compartments, periosteal (P) and endosteal (E), each having a time-dependent tissue concentration of dye, QP(t) and QE(t), respectively; where a region of interrogation is $\vec{r}$ and fitting parameters of the model to observed total concentration of dye versus time fits parameters PBF($\vec{r}$) representing periosteal blood flow, EBF($\vec{r}$) representing endosteal blood flow, TP($\vec{r}$) representing the arrival time of a dye bolus to periosteal vasculature centered under $\vec{r}$ MP($\vec{r}$) representing a minimum time required for dye to travel across the periosteal vasculature, TE($\vec{r}$) representing an arrival time of the dye bolus to the endosteal vasculature in the area of centered under $\vec{r}$ and permits calculation of total bone blood flow, TBF=PBF+EBF; and EBF.

6. The implant of claim 4 wherein the rigid plate or rod of the implant comprises ultra-high molecular weight polyethylene (UHMWPE).

7. The system of claim 2, where the bone-specific kinetic model models two tissue compartments, periosteal (P) and endosteal (E), each having a time-dependent tissue concentration of dye, QP(t) and QE(t), respectively; where a region of interrogation is $\vec{r}$ and fitting parameters of the model to observed total concentration of dye versus time fits parameters PBF($\vec{r}$) representing periosteal blood flow, EBF($\vec{r}$) representing endosteal blood flow, TP($\vec{r}$) representing the arrival time of a dye bolus to periosteal vasculature centered under $\vec{r}$ MP($\vec{r}$) representing a minimum time required for dye to travel across the periosteal vasculature, TE($\vec{r}$) representing an arrival time of the dye bolus to the endosteal vasculature in the area of centered under $\vec{r}$ and permits calculation of total bone blood flow, TBF=PBF+EBF; and EBF.

* * * * *